(12) United States Patent
Yang et al.

(10) Patent No.: US 8,389,498 B2
(45) Date of Patent: Mar. 5, 2013

(54) SPINNING SOLUTION AND METHOD FOR MANUFACTURING BIOMATERIAL FIBERS

(75) Inventors: Chan-Yi Yang, Taipei (TW); Jui-Sheng Lee, Tu-Chen (JP); Chih-Kang Peng, Tu-Chen (TW)

(73) Assignee: Taiwan Textile Research Institute, Tu-Chen, Taipei Hsien (TW)

( * ) Notice: Subject to any disclaimer, the term of this patent is extended or adjusted under 35 U.S.C. 154(b) by 309 days.

(21) Appl. No.: 12/732,358

(22) Filed: Mar. 26, 2010

(65) Prior Publication Data

US 2011/0237539 A1   Sep. 29, 2011

(51) Int. Cl.
*A61K 31/728* (2006.01)
*A61K 31/715* (2006.01)

(52) U.S. Cl. .................. 514/53; 514/54; 514/55

(58) Field of Classification Search .............. 514/53, 514/54, 55
See application file for complete search history.

(56) References Cited

U.S. PATENT DOCUMENTS

| | | | |
|---|---|---|---|
| 3,903,268 A | 9/1975 | Balassa | |
| 3,911,116 A | 10/1975 | Balassa | |
| 3,914,413 A | 10/1975 | Balassa | |
| 6,344,077 B1 * | 2/2002 | Hong | 106/162.2 |
| 2006/0134158 A1 * | 6/2006 | Majima et al. | 424/422 |
| 2007/0009578 A1 | 1/2007 | Moller et al. | |

FOREIGN PATENT DOCUMENTS

| | | | |
|---|---|---|---|
| CN | 1687498 A | * | 10/2005 |
| CN | 1952227 A | * | 4/2007 |

OTHER PUBLICATIONS

Yamane, S., et al.; "Feasibility of Chitosan-Based Hyaluronic Acid Hybrid Biomaterial for a Novel Scaffold in Cartilage Tissue Engineering;" Biomaterials 26; 2005; pp. 611-619.

* cited by examiner

*Primary Examiner* — Wu-Cheng Winston Shen
*Assistant Examiner* — Everett White
(74) *Attorney, Agent, or Firm* — McClure, Qualey & Rodack, LLP

(57) ABSTRACT

Disclosed herein are spinning solutions and methods for manufacturing a biomaterial fiber. The spinning solution includes a biologically absorbable material having a haemostatic function, a polysaccharide selected from the group consisting of hyaluronic acid (HA) and gelatin, and a solvent, wherein the polysaccharide and the haemostatic material exist in a weight ratio between about 0.1 to about 3. The method includes steps of wet spinning the spinning solution into the biomaterial fiber.

18 Claims, 1 Drawing Sheet

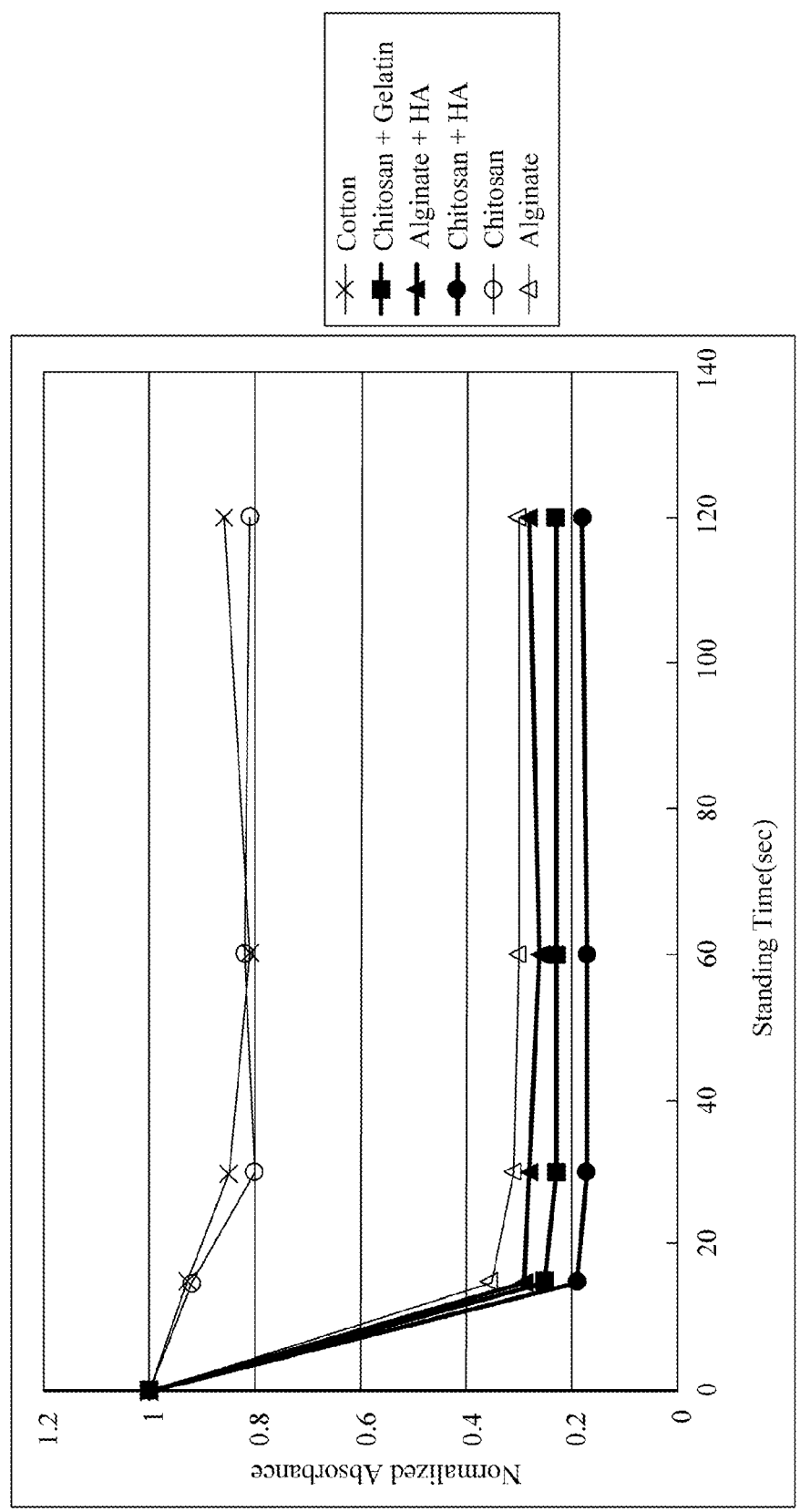

US 8,389,498 B2

SPINNING SOLUTION AND METHOD FOR MANUFACTURING BIOMATERIAL FIBERS

BACKGROUND

1. Field of Invention

The present invention relates to a spinning solution. More particularly, the present invention relates to a spinning solution for manufacturing biomaterial fibers, which may provide both haemostatic and wound healing function.

2. Description of Related Art

Stanching bleeding during surgery or from damaged organs or hemorrhage-prone wounds is important for the survival of patients. Many haemostatic materials have been developed such as U.S. Pat. Nos. 3,914,413, 3,911,116 and 3,903,268, and Patent Application Publication No. 2007/0009578.

Haemostatic sponges have been used in surgery for facilitating the arrest of bleeding. It is believed that the haemostatic effect of a sponge depends on sponge porosity and its ability in absorbing blood. A conventional gelatin sponge adheres to the bleeding site and absorbs a large amount of blood. Due to the porosity of a sponge, blood platelets are caught and the coagulation cascade, which stops the bleeding, is activated. However, when the sponge starts to absorb the blood, the volume of the sponge increase inevitably and thus is not suitable for some applications.

Haemostatic fleeces have also been found suitable for haemostasis and are successful on the market. These haemostatic products have a fleece-like structure and are generally consisted of collagen or gelatin. They have a high absorption capacity. During open surgery, these fleeces are lightly pressed on the wound by hand until the bleeding stops.

A haemostatic fiber consisting of hyaluronic acid (HA) and chitosan have been reported (Biomaterial 2005, 611-619, Sintaro Yamane et al.). In this technology, a pure chitosan fiber is formed first, and is then immersed in a HA solution to absorb HA. However, the HA merely diffuses into chitosan fiber in the vicinity of the surface, and it is difficult to control the content of HA in chitosan fiber, and a more complex process is required for producing the same. In addition, the inner chitosan material may be ineffective before the outer HA material is absorbed by the body.

In view of the above, there exists in this art a need of an improved biomaterial fiber and a method of producing the same.

SUMMARY

According to one aspect of the present disclosure, a spinning solution is disclosed. The spinning solution comprises a biologically absorbable material having a haemostatic function, a polysaccharide and a solvent; wherein the polysaccharide and the biologically absorbable material exist in the spinning solution in a weight ratio between about 0.1 to about 3.

According to one aspect of the present disclosure, a method for manufacturing a biomaterial fiber is disclosed. The method comprises the steps of: preparing the spinning solution described above, and wet spinning the spinning solution into the biomaterial fiber.

According to another aspect of the present disclosure, a biomaterial is also disclosed. The biomaterial comprises a plurality of fibers that are made by the method described above.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 1 illustrates the blood-clotting effects of samples respectively made from examples 1.1, 1.2 and 1.3 according to the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

According to one aspect of the present disclosure, a spinning solution is disclosed. The spinning solution comprises a biologically absorbable material having a haemostatic function, a polysaccharide and a solvent. The polysaccharide and the biologically absorbable material exist in the spinning solution in a weight ratio between about 0.1 to about 3.

According to another aspect of the present disclosure, a method for manufacturing a biomaterial fiber is disclosed. The method comprises the steps of: preparing the spinning solution described above, and wet spinning the spinning solution so as to obtain the biomaterial fiber.

In the spinning solution, if the weight ratio of the polysaccharide to the haemostatic material is greater than about 3, it is difficult to form a fiber in the wet spinning process.

In the present disclosure, the term "biologically absorbable" refers herein a material that can be degraded in the body to small molecules having a size that allows them to be transported into the blood system. In addition, the "hasmostatic" refers to an effect of enhancing the physiological blood coagulation process, and thereby reducing the time of forming a firm blood clot.

In one embodiment, the biologically absorbable material having the haemostatic function is chitosan, and the weight ratio of the polysaccharide such as hyaluronic acid (HA) and gelatin to the chitosan in the spinning solution is about 0.1 to about 1. In this embodiment, when the ratio of the polysaccharide to the chitosan is greater than about 1, gels may be observed in the spinning solution, and thus is unfavorable to the following wet spinning process. In particular, HA becomes an anion and chitosan becomes a cation in the spinning solution. The anionic HA and the cationic chitosan may combine together in the spinning solution, and thus forming the gel. The present disclosure discovers that the gel may not occur in the spinning solution when the weight ratio of the polysaccharide such as HA and gelatin to the chitosan is less than about 1. On the other hand, when the ratio of the polysaccharide to the chitosan is less than about 0.1, the effect of the polysaccharide such as hyaluronic acid (HA) and gelatin is unobvious. HA and gelatin may facilitate the wound healing, and thus the biomaterial fiber obtained from the spinning solution may provide both haemostatic and wound healing function. Moreover, the hyaluronic acid or gelatin added into chitosan may further improve the haemostatic effect of the biomaterial fiber, probably because the hyaluronic acid and gelatin may decrease the hydrophobic property of chitosan. In one example, the weight ratio of the polysaccharide such as hyaluronic acid and gelatin to the chitosan is in the range of about 0.2 to about 0.6.

In some examples, the concentrations of the polysaccharide and chitosan respectively are in the range of about 1%-5% and about 3%-10% by weight of the spinning solution, and the solvent in the spinning solution is water.

In another embodiment, the biologically absorbable material having the haemostatic function is alginate, and the weight ratio of the polysaccharide such as hyaluronic acid (HA) and gelatin to the alginate in the spinning solution is about 0.1 to about 1. In this embodiment, the biomaterial fiber is suitable for application in the haemostatic and wound healing usage. When the weight ratio of the polysaccharide to the alginate is greater than 1, the biomaterial fiber obtained from the spinning solution becomes too soft and is unfavorable to the application in haemostatic bandages. In one example, the weight ratio of the polysaccharide to the alginate is in the range of about 0.2 to about 0.6. In some examples, the concentration of the polysaccharide and alginate respectively may be about 1%-5% and about 3%-10% by weight of the spinning solution. In these examples, the solvent may be water.

In still another embodiment, the biologically absorbable material having the haemostatic function is alginate, and the weight ratio of the polysaccharide such as hyaluronic acid and gelatin to the alginate is in the range of about 1 to about 3. In this embodiment, the biomaterial fiber thus obtained is suitable for an anti-adhesion biomaterial since the fiber has a higher content of HA and/or gelatin.

In one embodiment, the step of wet spinning the spinning solution comprises extruding the spinning solution into a coagulation solution. In one example, the biologically absorbable material having the haemostatic function of the spinning solution is chitosan, and the coagulating solution comprises sodium hydroxide, methanol and water. More specifically, the coagulating solution may be a solution comprising about 5 wt % of sodium hydroxide, based on the total coagulating solution, dissolved in a solvent consisting of methanol and water with a weight ratio of 1:1. In another example, the biologically absorbable material having the haemostatic function of the spinning solution is alginate, and the coagulating solution comprises calcium chloride, ethanol and water. For example, the coagulating solution may comprise about 5 wt % of calcium chloride, based on the total coagulating solution, dissolved in a solvent consisting of ethanol and water with a weight ratio of 1:1.

In one embodiment, the method for manufacturing a biomaterial fiber described above may further comprise a drying step after the wetting spinning process to remove the solvent such as water and alcohol in the biomaterial fiber. For example, a vacuum drying process may be employed.

In the present disclosure, the biomaterial fiber is obtained by wet spinning the spinning solution comprising both polysaccharide and haemostatic material. The biomaterial fiber may be formed in a single step, and thus simplifying the manufacturing process. Furthermore, the biomaterial fiber substantially has a uniform concentration of polysaccharide such as HA and gelatin in the fiber.

In the prior art, a fiber comprising alginate and collagen has been disclosed. However, it needs a cross-linking process after wet spinning so as to improve the mechanical strength of the fibers. Compared to the prior art fiber, the fiber prepared by the method of the present disclosure no longer requires the cross-linking treatment. Furthermore, hyaluronic acid may provide a better effect of wound healing than collagen, probably because of the hyaluronic acid being associated with the cell migration whereas the collagen is associated with the cell adsorption.

According to another aspect of the present disclosure, a biomaterial is also disclosed. The biomaterial may comprise a plurality of fibers that is made by the method described above. For example, the biomaterial may be made from the biomaterial fibers through non-woven methods known in the art.

EXAMPLES

The following Examples are provided to illustrate certain aspects of the present invention and to aid those of skill in the art in practicing this invention. These Examples are in no way to be considered to limit the scope of the invention in any manner.

Example 1

1.1 Biomaterial Fiber Comprising HA and Chitosan 50 g of chitosan and 25 g of acetic acid ($CH_3COOH$) was mixed with 950 g water, and the mixture was stirred at room temperature for 3 hours until chitosan was completely dissolved. 25 g of HA was then added to form a spinning solution. A coagulating solution was independently prepared by mixing 50 g of sodium hydroxide (NaOH), 475 g of methanol, and 475 of water.

For wet spinning, the spinning solution was extruded from a spinning gear set at 1.5 ml/min into the coagulating solution through a spinning nozzle having 500 holes, wherein each hole has a diameter of 10 μm to form biomaterial fibers. The biomaterial fibers were placed in a vacuum dryer to remove the residual solvent such as water and methanol.

1.2 Biomaterial Fiber Comprising Gelatin and Chitosan

In this example, the biomaterial fibers were prepared by the same method as described in EXAMPLE 1.1, except the HA was replaced by gelatin.

1.3 Biomaterial Fiber Comprising HA and Alginate

In this example, 5 g of HA, 35 g of alginate and 950 g of water were mixed and stirred thoroughly to form the spinning solution. The coagulating solution was prepared by mixing 50 g of calcium chloride ($CaCl_2$), 475 g of ethanol, and 475 of water. The biomaterial fibers were prepared by the wet spinning and drying process as described in EXAMPLE 1.1.

The biomaterial fibers formed in Example 1 were further used to form a non-woven fabric, respectively.

Example 2

Characterization of the Biomaterial Fibers of Example 1

The blood-clotting effects of the biomaterial fibers of Example 1 were quantified by the following test. Briefly, 100 μL of blood was added onto a 0.1 g biomaterial sample made from the biomaterial fibers of EXAMPLE 1.1, 1.2 and 1.3, respectively. After standing a certain period of time, e.g. 15, 30, 60 and 120 seconds, the biomaterial sample having blood thereon was immersed in 10 ml saline in a container and shaken for 4 min. Unclotted blood on the biomaterial sample would be dissolved in the saline, whereas the clotted blood remained attached on the fabrics. After shaking, the biomaterial sample was removed from the saline, and the content of blood in the saline was quantified by enzyme-linked immunosorbent assay (ELISA), wherein the absorbance of the saline at a wavelength of 540 nm was measured by a Ultraviolet/Visible spectrometer. The lower the absorbance, the lower the concentration of blood in the saline, and a higher amount of clotted blood on the biomaterial sample would be. In addition, a standard solution was prepared by adding 100 µL of blood in 10 ml saline. The absorbance of the standard solution was also measured by the same spectrometer at the same wavelength. A normalized absorbance may be obtained by the following equation:

$$a_n = a_p/a_s;$$

wherein $a_n$ is the normalized absorbance; $a_p$ is the absorbance of the solution sample; and $a_s$ is the absorbance of the standard solution.

FIG. 1 depicts the blood-clotting effects of biomaterial samples made from the biomaterial fibers of EXAMPLE 1.1, 1.2 and 1.3, respectively; wherein a cotton sample was used as a reference. The saline associated with the biomaterial sample comprising HA and chitosan of EXAMPLE 1.1 exhibits the lowest normalized absorbance of about 0.18 at 15 second of standing time, which implies that about 82% of blood was clotted on the biomaterial sample at 15 second of standing time. By comparing to the result of the saline of the controlled cotton sample, which shows a high absorbance of about 0.92, the biomaterial sample of EXAMPLE 1.1 significantly enhances the blood coagulation process. Furthermore, the biomaterial samples of EXAMPLE 1.2 and EXAMPLE 1.3 also show similar results.

FIG. 1 also illustrates the blood-clotting effects of biomaterial samples made from pure chitosan and pure alginate, respectively. The saline associated with pure chitosan exhibits a normalized absorbance of about 0.9 at 15 seconds of standing time, which implies that only about 10% blood was clotted on the pure chitosan sample at 15 second of standing time. Compared to the results of EXAMPLE 1.1 and EXAMPLE 1.2, HA and gelatin may considerably improve the haemostatic property of chitosan. In addition, the saline associated with pure alginate sample exhibits a normalized absorbance of about 0.36 at 15 seconds of standing time. The biomaterial comprising alginate and HA of EXAMPLE 1.3 has a better haemostatic property than pure alginate.

Example 3

Wound-Healing Effect of the Biomaterial Fibers of Example 1

The wound-healing effects of the biomaterial fibers of Example 1.1 were quantified by the following test. Briefly, two wounds were formed on the skin of a male ICR mouse, each of the wounds having an area of 4 cm². Subsequently, one of the two wounds was treated by the non-woven fabric of Example 1.1, whereas the other one was treated by a commercial product of KALTIOSTAT™ as a reference. After a certain period of time, e.g. 7, 14 and 21 days, each of the area of the wounds were measured independently, and the results were summarized in Table 1.

TABLE 1

|  | Example 1.1 (Chitosan + HA) | KALTIOSTAT ™ |
| --- | --- | --- |
| initial | 4 cm² | 4 cm² |
| 7 days | 4 cm² | 4 cm² |
| 14 days | 2 cm² | 3 cm² |
| 21 days | 0.2 cm² | 0.5 cm² |

The biomaterial fibers of Example 1.1 exhibits an excellent effect on the would healing. As illustrated in table 1, after 14 days of treatment, the wound treated by the non-woven fabric of Example 1.1 had an area of 2 cm², while the wound treated by KALTIOSTAT™ had an area of 3 cm². After 21 days of treatment, the wound treated by the non-woven fabric of Example 1.1 healed and the area of the wound reduced to only 0.2 cm², whereas the wound treated by KALTIOSTAT™ still had an area of 0.5 cm².

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A spinning solution, comprising:
   a biologically absorbable material having a haemostatic function;
   hyaluronic acid; and
   a solvent;
   wherein hyaluronic acid and the biologically absorbable material exist in the spinning solution in a weight ratio between about 0.1 to about 3.

2. The spinning solution according to claim 1, wherein the biologically absorbable material having the haemostatic function is selected from the group consisting of an alginate and a chitosan.

3. The spinning solution according to claim 2, wherein the biologically absorbable material having the haemostatic function is chitosan, and thereby rendering the weight ratio of hyaluronic acid and chitosan to be in the range of about 0.1 to about 1.

4. The spinning solution according to claim 3, wherein the weight ratio of hyaluronic acid and chitosan is in the range of about 0.2 to about 0.6.

5. The spinning solution according to claim 4, wherein hyaluronic acid has a concentration of about 1-5% by weight of the spinning solution.

6. The spinning solution according to claim 5, wherein chitosan exists in a concentration of about 3-10% by weight of the spinning solution.

7. The spinning solution according to claim 2, wherein the biologically absorbable material having the haemostatic function is alginate.

8. The spinning solution according to claim 7, wherein the weight ratio of hyaluronic acid and alginate is in the range of about 0.1 to about 1.

9. The spinning solution according to claim 8, wherein the weight ratio of hyaluronic acid and alginate is in the range of about 0.2 to about 0.6.

10. The spinning solution according to claim 7, wherein hyaluronic acid has a concentration of about 1-5% by weight of the spinning solution.

11. The spinning solution according to claim 10, wherein the alginate has a concentration of about 3-10% by weight of the spinning solution.

12. The spinning solution according to claim 7, wherein the weight ratio of hyaluronic acid and alginate is in the range of about 1 to about 3.

13. The spinning solution according to claim 1, wherein the solvent is water.

14. A method for manufacturing a biomaterial fiber, comprising:
    wet spinning the spinning solution of claim 1 into the biomaterial fiber.

15. The method according to claim 14, wherein the step of wet spinning comprises extruding the spinning solution into a coagulation solution.

16. The method according to claim 15, wherein the biologically absorbable material having the haemostatic function is chitosan, and the coagulating solution comprises sodium hydroxide, methanol and water.

17. The method according to claim 15, wherein the biologically absorbable material having the haemostatic function is alginate, and the coagulating solution comprises calcium chloride, ethanol and water.

18. A biomaterial comprising a plurality of fibers made by the method set forth in claim 14.

* * * * *